(12) United States Patent
Zavala et al.

(10) Patent No.: US 9,220,804 B2
(45) Date of Patent: Dec. 29, 2015

(54) FEMALE SANITARY AND INCONTINENCE TOWELS, GAUZE/BANDAGES AND SURGICAL DRESSINGS FOR TREATING WOUNDS BASED ON TOURMALINE

(71) Applicants: Jose Zavala, Cudahy, CA (US); Gabriel C Damian, Anaheim Hills, CA (US)

(72) Inventors: Jose Zavala, Cudahy, CA (US); Gabriel C Damian, Anaheim Hills, CA (US)

( * ) Notice: Subject to any disclaimer, the term of this patent is extended or adjusted under 35 U.S.C. 154(b) by 75 days.

(21) Appl. No.: 13/939,267

(22) Filed: Jul. 11, 2013

(65) Prior Publication Data

US 2014/0330231 A1  Nov. 6, 2014

(30) Foreign Application Priority Data

May 2, 2013  (MX) ................. MX/a/2013/004986

(51) Int. Cl.
| | |
|---|---|
| *A61F 13/15* | (2006.01) |
| *A61F 13/20* | (2006.01) |
| *A61L 15/18* | (2006.01) |
| *A61L 15/24* | (2006.01) |
| *A61L 15/40* | (2006.01) |

(52) U.S. Cl.
CPC ................. *A61L 15/18* (2013.01); *A61L 15/24* (2013.01); *A61L 15/40* (2013.01); *A61L 2400/12* (2013.01)

(58) Field of Classification Search
USPC ................. 604/367, 359–360, 375, 377–378
See application file for complete search history.

(56) References Cited

U.S. PATENT DOCUMENTS

| | | | | |
|---|---|---|---|---|
| 4,673,402 | A * | 6/1987 | Weisman et al. | 604/368 |
| 5,217,445 | A * | 6/1993 | Young et al. | 604/381 |
| 5,387,208 | A * | 2/1995 | Ashton et al. | 604/378 |
| 8,821,467 | B1 * | 9/2014 | Minella | 604/385.15 |
| 2008/0015532 | A1 * | 1/2008 | Waksmundzki | 604/378 |
| 2014/0121625 | A1 * | 5/2014 | Kirby et al. | 604/383 |

FOREIGN PATENT DOCUMENTS

EP  2 111 833 A1 * 10/2009 ............ A61F 13/472

* cited by examiner

*Primary Examiner* — Michele M Kidwell
(74) *Attorney, Agent, or Firm* — Defillo & Associates, Inc; Evelyn A. Defillo (57) ABSTRACT

A surgical use, healing, and personal hygiene devices, in which, among other components, includes: a first layer of bamboo fibers or organic cotton, adapted to stay in contact with the skin of a user; a layer of non-woven fabric having in a central place an element made of polypropylene and thermostable elastomers fibers, in which is absorbed a nanometric tourmaline powder; and a layer opposite to the first layer including materials that allow "ventilation" to the device and, at the same time, form a moisture barrier. Also describes the use of nano tourmaline powder in these applications.

3 Claims, 7 Drawing Sheets fig 1 fig 2 fig 3 fig 4 fig 5 fig 6 fig 7

US 9,220,804 B2

FEMALE SANITARY AND INCONTINENCE TOWELS, GAUZE/BANDAGES AND SURGICAL DRESSINGS FOR TREATING WOUNDS BASED ON TOURMALINE

FIELD OF THE INVENTION

The present invention relates to personal hygiene and surgical medical devices, especially female sanitary towels, surgical dressings for the care and treatment of wounds; urinary incontinence devices, etc., all of them having tourmaline, as well as to the use of this mineral in those fields.

BACKGROUND OF THE INVENTION

Women are susceptible to a large number of bacterial and fungal infections of the genitourinary area, especially during their menstrual period. It has been discovered that a female towel after some hours of use, may be contaminated (up to 107 bacteria per $cm^2$), due to the easy contamination and poor quality of the raw material that manufacturers of these devices use, such as plastic, cellulose fiber, and non-woven fabric that are treated and bleached with chemicals, which are being in contact with the delicate skin cause an imbalance in the vulvovaginal pH. These and other types of pathogenic microorganisms may affect the cavities, the mucous, and the skin, for example, in burns, excoriations, trauma, injury and post-surgery processes sites, and other similar sites, also because, in good part, to the same problem, pH imbalance in the skin for using bandages, gauze, and dressings with the same quality standards mentioned above.

BRIEF DESCRIPTION OF THE INVENTION

In view of the above-identified situations, Applicant has been developing a material that may be used on different surgical, sanitary, and personal hygiene devices, especially feminine sanitary towels, gauze, bandages, dressings for the care and handling of surgical wounds, disposable surgical devices, urinary incontinence towels, diapers, etc.

In a first aspect, the invention refers to a female sanitary towel or a female sanitary pad, formed by a plurality of layers, with high quality materials in order to keep the vaginal pH to an optimum value of 3.80 to 4.29 (acid pH). The last layer of towel which is constituted by a permeable material that allows the passage and the presence of oxygen, a contributing factor in the elimination of anaerobic bacteria. If you have the following vaginal symptoms (itching, burning, bad odor, or unusual discharge) they are probably caused by an infection. If your symptoms appear, persist or worsen by using and maintaining a contaminated towel, of poor quality, you probably need medical treatment. Your doctor may suggest changing the brand of your feminine towel for a better quality one.

It needs to be mentioned that only your doctor may diagnose a vaginal infection by using a combination of: pH, microscopic examination of vaginal discharge, amine odor, cultivation, wet preparation, and Gram stain.

The materials used for a sanitary towel or a sanitary pad have the characteristic of including a material that, by convenience, will be named here as "chip", formed by a heat-stable polypropylene elastomer material, highly hydrophilic that contains finely divided nanometer size tourmaline powder.

In other aspects, the invention is also directed to other surgical, sanitary and medical and personal use products, as well as for urinary incontinence, formed also from the super absorbent polymer, polypropylene, thermostable elastomers, and tourmaline.

In the aspect of surgical application and/or for the care of injuries and similar, the invention as a whole provides an effective antibacterial effect, balancing the skin pH, reducing the skin irritation, inflammation, relieves itching and eliminates the peculiar smell caused by some bacteria.

Due to the capacity of the super absorbent polymer (SAP), it helps to decrease the amount of exudate, keeping the wound drier, allowing that the dressing can remain longer in place, for which the healing changes are just a function of the amount of the exudate.

The functional characteristics of these devices helps with the healing of contaminated and moist wounds.

BRIEF DESCRIPTION OF DRAWINGS

A detailed description of the invention will be discussed later on, which will be used as a support to the attached drawings, which form an integral part of this specification, and in which.

DESCRIPTION OF THE PREFERRED EMBODIMENT

The products of the different aspects of the present invention have a laminated structure, i.e., are composed of several layers arranged in a certain order. In each of the embodiments of the first aspect of the invention, i.e., those that refer to towels or sanitary pads will be given a description related to the number and the order in which these layers are arranged.

For now, it is suffice to say that in each aspect of the invention there is a special layer "chip", formed by a polypropylene material, heat stable elastomer and highly hydrophilic in which is present a tourmaline powder of nanometric size finely pulverized by trommels (calcination and concretion), embedded in the raw material liquefied of polypropylene and thermostable elastomers.

The formation of these layers is based on non-woven fibers, whose manufacture begins with the tromelado of the tourmaline to form a finely pulverized dust of nanometric size. Then, undergoes machining steps, electrode formation, that is, the application directs the current field to guide the dipoles and induce piezoelectricity. The fiber with the permanent electrode containing the substance of permanent electrode highly oriented and distributed on the surface of the fiber layer, may also be formed by evenly mixing and dispersing of 1 to 5 percent by weight of the permanent electrode substance, natural or artificial, powdered, in up to 1 gallon of liquefied raw material, such as polypropylene and thermostable elastomers. These materials, with the tourmaline, which is a natural mineral, melt to a mixed fiber or a filter material, by spinning.

This tourmaline material is present in the above-described structure and, for convenience, is called hereafter "tourmaline chip". The "chip" is a non-woven fabric made of a mixed fiber, which is mixed with the polypropylene and the thermostable elastomers to form the chip, which is intended to increase the mechanical property of the structure (hydrophilic effect) and to provide an outstanding permeability. The polypropylene and the thermostable elastomers, with intermediate crosslink densities, are the perfect type of crosslinking. In fact, the crosslinking is a critical structural factor (covalent bond) that contributes the fiber (the chip) to improve the impregnation of the fiber with tourmaline, and an emission of anions up to 5,950 per cubic centimeter, and a photon energy in the far-infrared.

As you will later appreciate in the description of each of the embodiments of the invention, the tourmaline "chip" is located in a specific site of the respective structure. In the case of the embodiments of towel or sanitary pad, the tourmaline "chip" is located in the center of the towel surface or sanitary pad, internally with regard to the body contact surfaces and opposite to the contact with the body. The proportion of the length and the width of the tourmaline layer with respect to the length and width of the towel or sanitary pad, is on the scale of ½ to ⅔, and, preferably, occupies the second layer of the sanitary pads/towels of the present invention.

On the other hand, the method of production of fiber materials of the present invention comprises in preparing the first material, containing a first chip of polypropylene, in an amount equivalent to around 70-95 percent in gross weight, with a molecular weight of 3.15×105 g/mol, or first chip of polyethylene with a molecular weight of around 1.5 to 2.5×105 g/mol (the preferred embodiments that are described in the following tests are based on the first polypropylene, which is present in about 80 percent of the raw material), and a portion of nanometric tourmaline that is present in around 5 to 30 percent in gross weight; as well as the thermostable elastomers that form around 1 to 40 percent of the gross weight. The first material is laminated to an agglomerated, and the second chip of polypropylene, with a molecular weight of 3.15×105 g/mol, or the second chip of polyethylene with a molecular weight of around of 1.5×2.5×105 g/mol, is taken as the second material. Of them, the content of tourmaline agglomerate is around 1 to 10 percent of the gross weight.

Then, the agglomerate and the second material are melted to spin, cool, thermally stretch, and form the fibers. The spinning temperature varies between around 200° C. to 300° C. (in the preferred mode of the present invention, spinning temperature varies between about 200° C. and 250° C. for the polypropylene, and between about 250° C. to 300° C. for the polyethylene); extensibility times are around 3 to 8, thermally stretching temperature is around 130° C. to 160° C. (100° C., the preferred mode of the present invention), and thermal formation temperature is around 70° C. to 100° C. (90° C. in the preferred modality of the present invention). Then, the nanometric tourmaline fiber/polypropylene or polyethylene is a spool, and is woven into a nanometric tourmaline fiber/polypropylene or polyethylene filter, by means of a knitting machine (stainless steel pipe in the present invention shuttle), whose longitudinal density is around 35 to 50 threads/inch, a latitudinal about density of 30 to 40 threads/inch and a fabric width of 65° C.

The filter materials made of fiber (mainly based on polypropylene) have stronger mechanical properties; the tensile strength declines gradually as the longitudinal strength of the fiber increases (from 41.17 kgf/cm$^2$ to 37.21 kgf/cm$^2$). This is, possibly, because the rigid tourmaline powder is embedded to the fiber structure of the polypropylene and the thermostable elastomers, by means of fusion and spinning, so that the rigidity of the anion/polypropylene fiber improves, but some anion generates particles in fiber, which can damage the resistance of the fiber. Thus, the tensile strength is diminished by increasing the amount of particles.

As you can see from the above, it is the objective of the present invention to provide a mixed structure of porous fiber/chip in the center of the pad, to help to quickly guide the fluid to the deepest section and increase the mechanical property (hydrophilic effect) and outstanding permeability. The polypropylene structure and thermostable elastomers, with intermediate crosslink densities, is the perfect type of entanglement. In fact, the interlacing is a critical structure factor (covalent bond) that contributes to the fiber (chip) to improve impregnation of the tourmaline fiber and the emission of anions and in the far-infrared.

To apply this new process to fabrics to medical devices, such as female sanitary towels/pads, gauzes, bandages or surgical and wound care dressings, skin care protectors, disposable adults, babies and preterm diapers, guards and pads for bladder control, pads and protectors for incontinence, underpants and diapers, folded gauze diapers, training underpants, panties, underwear, bathing suits, maternity protectors, OB pillows, tampons, and any type of disposable medical bandages, isolation masks and disposable protectors, as well as for all types of disposable surgical supplies.

Polypropylene is the principal polymer used in non-woven materials, with more than 50 percent used for diapers or sanitary products, which is treated to absorb water (hydrophilic) rather than naturally to repel the water (hydrophobic).

A polypropylene (joined by spinning) has been combined with non-woven blown structures by melting, conforming a stratified product called SMS (spinning-melting-spinning). The non-woven materials blown by melting have extremely fine fiber diameters, but are not strong fabrics. The spinning knitting binds either by using resins or thermally.

Some of the advantages of the present invention products are the following:
 Promotes the issuance of anions, up to 5,950 negative ions per cm$^3$ and emits photons in the far-infrared.
 Are antibacterial, reduce irritation, itching, burning, bad odor or unusual flow, inflammation, and are suitable for menstrual disorders.
 Contact dermatitis.
 Promotes the uterine detoxification.
 Assists in the elimination of diverse genitourinary problems.
 Balances the pH of mucous membranes and skin.
 The absorbent materials used comprise a chlorine-free polymer gel, which is known as "SAP" (super absorbent polymer).

Super absorbent polymers (SAP) retain water within the molecular chains and hold the water even under pressure. The absorption capacity of the super absorbent polymer is determined by the osmotic pressure, the affinity and elasticity of the polymers. The osmotic pressure has the maximum impact on the absorption capacity. Since menstrual blood is around 55 percent of plasma and the plasma is about 90 to 92 percent water, which makes the blood around 50 percent water, the products of the present invention are extremely suitable to retain body liquids, no matter how abundant they are.

Finished products present, in addition, other advantages and features that can be summarized as follows:
 Provide purely physical effects, are free from drugs, free of chemicals substances, and lack of side effects.
 The bottom layer (which is opposed to the body contact) allows for ventilation and is leak-proof. This layer allows air flow through the towel and at the same time acts as a barrier to moisture. The result is exceptional dryness and comfort for the skin.

Are extremely effective, fast-acting, and are not harmful.

Are not allergic. Users with gluten allergies or Celiac's disease will not be affected by the ingredients. Gluten is a mixture of proteins found in wheat, rye, barley, and oats. None of these proteins is used in the products of the invention.

Before giving practical examples of different sanitary and medical constructions in accordance with the invention, it is necessary to clarify that the description of these constructions, which will be based on the figures in the attached drawings, ordinal numbers will be used to designate the layers that make up each construction. The first layer will always be more up in the drawings, that is, the layer that is in contact with the user's body.

As can be seen from the drawings, sanitary towels formed in accordance with the invention are ergonomic and, among other features, preferably have nine layers. These layers are. The first layer is a layer of bamboo or organic cotton, with side edges, designed to prevent side spillage and make absorption to dry faster and prevent moisture, giving better absorbency and give a superior comfort. The second layer is distinctive because in the center it includes the chip of tourmaline, which is formed, as stated before, with a non-woven fabric of polypropylene fibers and thermostable elastomers, impregnated with the finely divided tourmaline. This chip of tourmaline, strategically perforated helps so the menstrual fluid quickly penetrates to the inside of the towel and increases the hydrophilic effect, providing outstanding permeability and producing emission of anions, to 5,950 negative ions per cubic centimeter, and photons in the far-infrared.

The third layer is a layer of air laid paper, which, given that it is tightly wrapped in the 360-degree, does not cause deformities or pollution in the sanitary towel.

The fourth layer, also air laid paper, increases the freshness and provides maximum absorbency to the sanitary towel.

The fifth layer is a super absorbent polymer (SAP). Since the super absorbent polymer (SAP) retains water within their molecular chains, even under pressure, the fifth layer is intended to absorb an amount of fluid that is mainly determined by the osmotic pressure.

The sixth and seventh layers are similar to the fourth layer and have the same purpose as that.

The eighth layer is an innovative support plate that allows air flow to the products of the invention through the sanitary towel, and at the same time acts as a hydrophobic barrier for the menstrual fluids preventing and protecting the staining of the intimate clothes and clothes in general. The result is exceptional dryness and comfort for the skin.

Finally, the ninth layer is formed by a plurality of lines of adhesive material (in this case, 10), which facilitates the assembly and the permanence of the sanitary towel with relation to the intimate clothes. This adhesive material is a food-grade adhesive.

In addition, a removable wax paper is present to protect the adhesive until the use of a sanitary towel.

Figure 1:
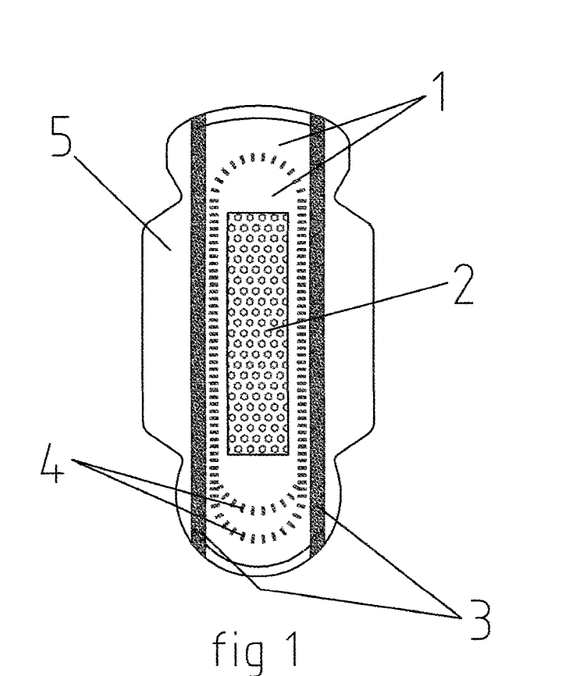
FIG. 1 is a schematic longitudinal view of a towel or sanitary pad for daytime use, in accordance with this invention.
Figure 2:
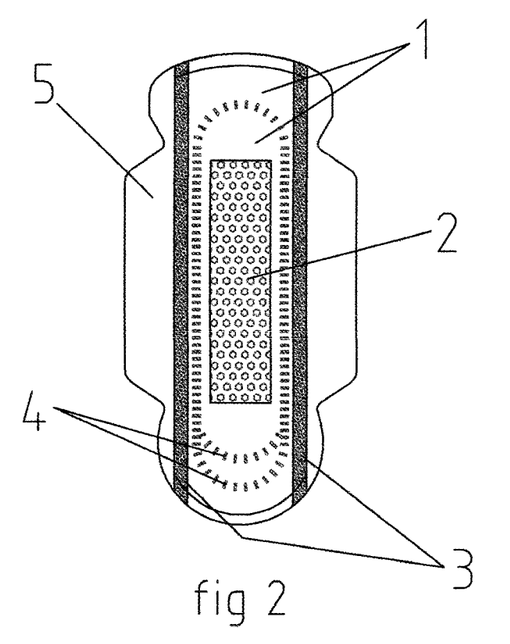
FIG. 2 is a schematic longitudinal view of a towel or sanitary pad for night use, in accordance with this invention.
Figure 3:
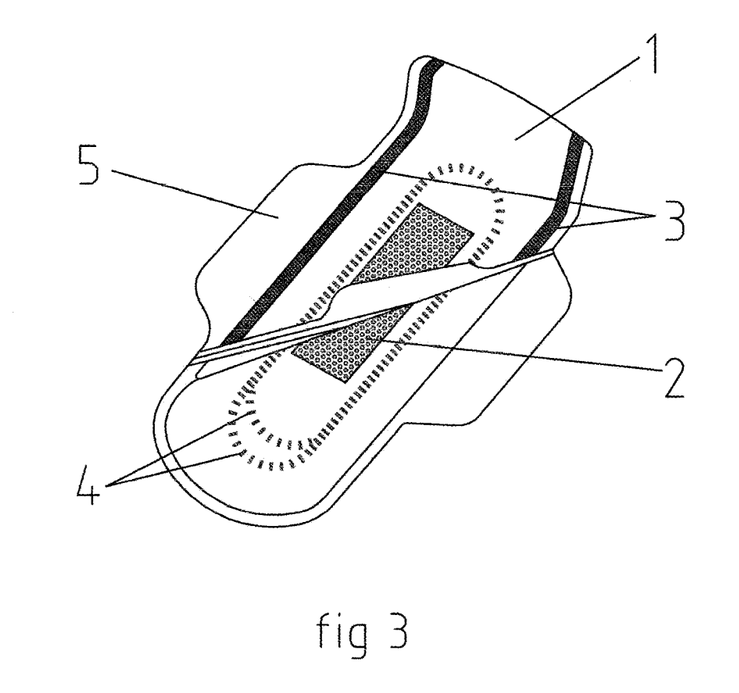
FIG. 3 is a schematic longitudinal view of a towel or sanitary pad for daytime use, in accordance with the invention.

FIGS. 1, 2 and 3 show three variations in the form of a sanitary towel in accordance with the invention. FIG. 1 shows a sanitary towel suitable for daytime use, whose preferred dimensions are from around 230 to 240 mm in length; FIG. 2 illustrates a sanitary towel for nighttime use, whose preferred dimensions are around 270 to 280 mm in length; FIG. 3 illustrates a panty protector, whose length is 155 to 165 mm.

In FIGS. 1 and 2, the number 1 designates the top layer, that is, the layer that stays in contact with the body of the user; it is made up of bamboo or organic cotton material. Number 2 indicates the chip of tourmaline, i.e., the portion of non-woven-based fabric based on polypropylene fibers and thermostable elastomers, impregnated with the finely divided tourmaline. Number 3 indicates the barriers or side selvedge, for leak prevention, while the number 4 indicates the rear side or the support, which is opposite to the number 1, where they are formed double channels for adjustment form, linked together and designed for protection against leakage. Finally, number 5 indicates the fins of the sanitary towel.

Figure 4:
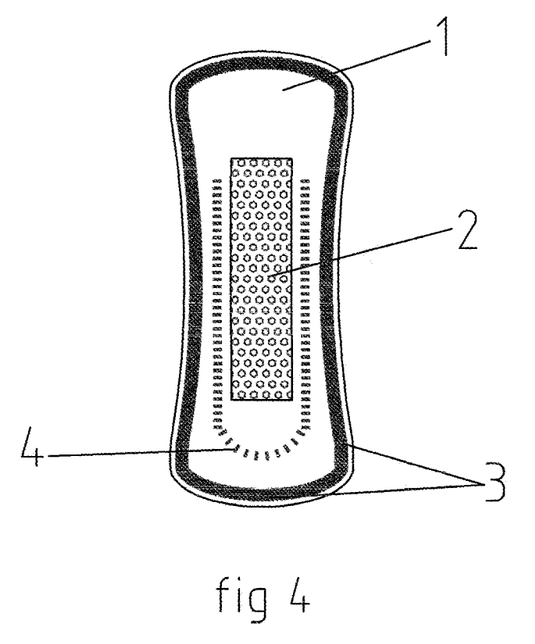
FIG. 4 is a schematic longitudinal view of a protective panty built in accordance with the present invention.

FIGS. 3 and 4 show a panty protector. In this Figure, numbers 1 to 4 correspond to the same numbers of FIGS. 1 and 2, with the same characteristics, but in the case of FIG. 4 there are no flaps.

Figure 5:
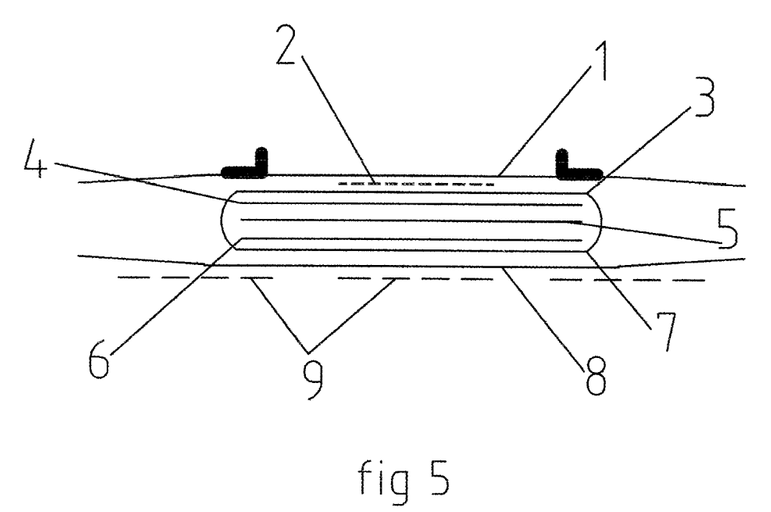
FIG. 5 is a cross-sectional view of a towel or sanitary pad in accordance with this invention for indiscriminate daytime or nighttime use.

FIG. 5, on the other hand, illustrates a cross-sectional view of the sanitary towel in accordance with the invention, suitable for the indistinct use, daytime or nighttime, where again number 1 indicates the first layer is identical to the FIGS. 1 to 3; number 2 also indicates the second layer, which is identical to the FIGS. 1 to 3. Number 3 indicates a third layer, of paper, like the fourth layer, identified with the number 4. Number 5 shows the fifth layer, formed by the super absorbent polymer, while with the numbers 6 and 7 are the sixth and seventh layers, respectively, also of paper. Number 8 refers to the back sheet or support which, although it allows the ventilation of the towel, acts as a barrier to moisture, prevents the introduction of contaminants and helps to protect the intimate garment and clothing in general. Finally, identified as number 9, the ninth layer, which comprises ten lines of adhesive material, to secure and maintain the position of the towel in the intimate cloth. Additionally, includes a sheet of waxed paper (not shown) over the ninth layer to protect the adhesive, and is removable at the time of use to secure the towel in the respective intimate cloth.

With regard to the second aspect of the invention that refers to medical use and surgical devices and treatment materials, especially gauzes, bandages and dressings, these products are preferably formed from the same eight top layers that were previously described in the present invention, eliminating the ninth of those layers, since the adhesive is not necessary to attach the device. Each one of these eight layers has the same physical and functional characteristics previously mentioned. The form, on the other hand, varies, as it is preferred to be rectangular, and two preferred sizes: the first of them, 20×8 cm, and the second, 20×13 cm.

It should be noted that in US hospitals the nosocomial infection rates average between 2 and 3 percent, and that one of every six US patients experience infections in the surgical site (SSI); and these SSI prolongs the hospital stay in more than six days and therefore increases the costs up to US $3,089.00. By this reason, it was designed a series of surgical devices and treating materials for wound care according to the principles of the invention, specifically designed for post-surgery applications, in order to fight infection at the surgical site (SSI), take care of wounds and prevent pressure ulcers.

Two circumstances are to be considered: the first is that, when there is friction and pressure on the tourmaline "Chip" the chip releases a large amount of negative ions and, at the same time, emits far-infrared rays. Therefore, inclusion in the materials of this second aspect of the invention, of the polypropylene, thermostable elastomers and the tourmaline, has great activity and a strong effect of reduction-oxidation (redox), which is capable of damaging the bacterial cell membrane or the enzyme activity in the cell protoplasm, with a bactericidal effect. A dressing that includes polypropylene fibers and thermostable elastomers impregnated with tourmaline, not only gives basic protection to a wound, but it also creates an optimal healing environment balancing pH to intensify the re-epithelization, but without over-saturation in dermal wound edges.

Figure 6:
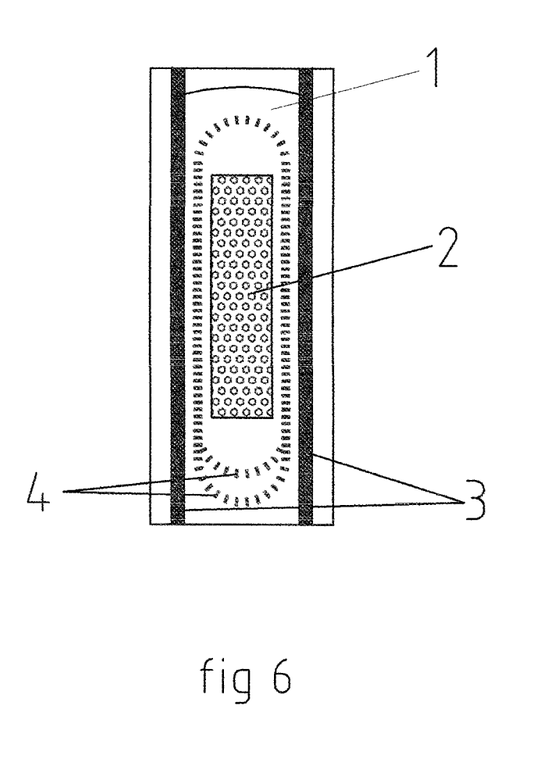
FIG. 6 is a schematic longitudinal view of a dressing formed in accordance with the principles of the invention.

FIG. 6 gives an example of a dressing formed in accordance with the principles of the present invention. That figure indicates as number 1 the top layer, similar to the first layer of the varieties of the first aspect of the invention, the same as the second layer, marked with the number 2, which contains tourmaline chip. The number 3 indicates the side rails to prevent leaks, and number 4 is the rear side or support, with form adjustment channels, of double-width, linked together and designed for protection against leaks.

Figure 7:
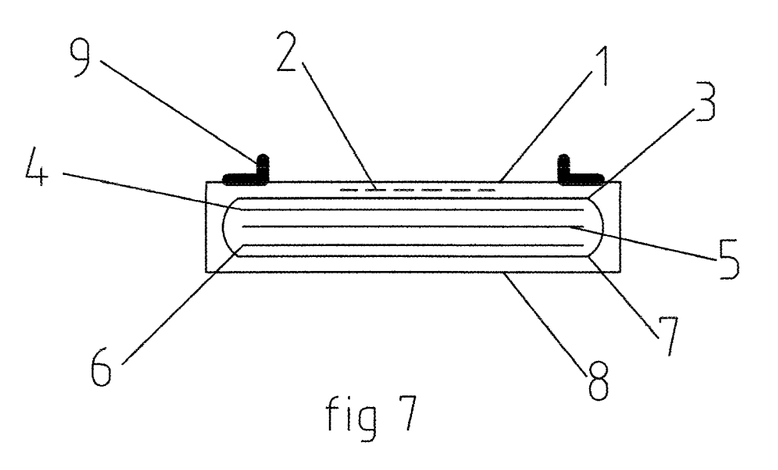
FIG. 7 is a cross-sectional view of the dressing in accordance with FIG. 6.

FIG. 7 shows the same dressing, but in a cross-sectional view, and the numbering refers to the order of the layers. Again, the first layer is the layer in contact with the body. It then outlines the series of layers of the element of this second aspect of the invention:

First layer: layer of bamboo or organic cotton.
Second layer: provides the chip of tourmaline in the center of the dressing.
Third layer: Paper, with tight wrapping of 360 degrees.
Fourth layer: Paper, provides maximum absorbency.
Fifth layer: SAP, super absorbent polymer.
Sixth layer: Paper, provides maximum absorbency.
Seventh layer: Paper, with tight wrapping of 360 degrees.
Eighth layer: support sheet that acts as a barrier to moisture, but allows the ventilation of the element, prevents the entry of contaminants, and protects clothing.
Ninth layer: Lateral selvedges to prevent moisture.

Although it has been described and illustrated in the foregoing, some modalities of the invention, nothing as described and illustrated, have been to restrict the scope of the invention, but merely to illustrate its characteristics in an understandable way. Therefore, the invention will only be restricted by the spirit of broad claims that come here.

What is claimed is:

1. A sanitary device for personal hygiene and for surgical use and healing materials consisting of:
   a plurality of layers in the following order:
   a first layer adapted to be in contact with a skin of a user, the first layer is made of fibers of bamboo or an organic cotton;
   a second layer after the first layer, the second layer is made of a non-woven fabric with porous fibers;
   a perforated element located on the second layer, the perforated element is made of an intermediate cross link density polypropylene, a polyethylene polymer, and an intermediate cross link density thermostable elastomers and impregnated with nanometric size tourmaline powder;
   a third layer after the perforated second layer, the third layer is made of an air laid paper;
   a fourth layer after the third layer, the fourth layer is made of an air laid paper;
   a fifth layer after the fourth layer, the fifth layer is made of a chlorine-free super absorbent polymer;
   a sixth layer after the fifth layer, the sixth layer is made of an air laid paper;
   a seventh layer after the sixth layer, the seventh layer is connected to the third layer forming a 360 degrees tight wrap that encloses the fourth, fifth, and sixth layers, the seventh layer is made of an air laid paper;
   an eighth layer after the seventh layer, the eighth layer is a support layer made of a breathable material;
   a ninth layer after the eighth layer, the ninth layer is made of an adhesive material;
   wherein when there is friction and pressure, the perforated element emits about 5,950 negative ions per cubic centimeter and photons in the far-infrared
   wherein the sanitary device is selected from the group consisting of a feminine sanitary towel, an underwear protector, an incontinence device, a surgical use device or a healing device.

2. A sanitary device for personal hygiene and for surgical use and healing materials consisting of:
   a plurality of layers in the following order:
   a first layer including side wings adapted to be in contact with a skin of a user, the first layer is made of fibers of bamboo or an organic cotton;
   a second layer after the first layer, the second layer is made of a non-woven fabric with porous fibers;
   a perforated element located on the second layer, the perforated element is made of an intermediate cross link density polypropylene, a polyethylene polymer, and an intermediate cross link density thermostable elastomers and impregnated with nanometric size tourmaline powder pulverized by trommels;
   a third layer after the perforated second layer, the third layer is made of an air laid paper;
   a fourth layer after the third layer, the fourth layer is made of an air laid paper;
   a fifth layer after the fourth layer, the fifth layer is made of a chlorine-free super absorbent polymer;
   a sixth layer after the fifth layer, the sixth layer is made of an air laid paper;
   a seventh layer after the sixth layer, the seventh layer is connected to the third layer forming a 360 degrees tight wrap that encloses the fourth, fifth, and sixth layers, the seventh layer is made of an air laid paper;
   an eighth layer after the seventh layer, the eighth layer is a support layer made of a breathable material;
   a ninth layer after the eighth layer, the ninth layer is made of an adhesive material;
   wherein when there is friction and pressure, the perforated element emits about 5,950 negative ions per cubic centimeter and photons in the far-infrared.

3. A sanitary device for personal hygiene and for surgical use and healing materials consisting of:
   a plurality of layers in the following order:
   a first layer adapted to be in contact with a skin of a user, the first layer is made of fibers of bamboo;
   a second layer after the first layer, the second layer is made of a non-woven fabric with porous fibers;
   a perforated element located on the second layer, the perforated element is made of an intermediate cross link density polypropylene, a polyethylene polymer, and an intermediate cross link density thermostable elastomers and impregnated with nanometric size tourmaline powder;
   a third layer after the perforated second layer, the third layer is made of an air laid paper;
   a fourth layer after the third layer, the fourth layer is made of an air laid paper;
   a fifth layer after the fourth layer, the fifth layer is made of a chlorine-free super absorbent polymer;
   a sixth layer after the fifth layer, the sixth layer is made of an air laid paper;
   a seventh layer after the sixth layer, the seventh layer is connected to the third layer forming a 360 degrees tight wrap that encloses the fourth, fifth, and sixth layers, the seventh layer is made of an air laid paper;

an eighth layer after the seventh layer, the eighth layer is a support layer made of a breathable material;
a ninth layer after the eighth layer, the ninth layer is made of an adhesive material;
wherein when there is friction and pressure, the perforated element emits about 5,950 negative ions per cubic centimeter and photons in the far-infrared.

* * * * *